US00PP32409P2

(12) United States Plant Patent
Lommerse et al.

(10) Patent No.: US PP32,409 P2
(45) Date of Patent: Oct. 27, 2020

(54) ***ALLIUM* PLANT NAMED 'AVAT88'**

(50) Latin Name: *Allium tanguticum*
Varietal Denomination: Avat88

(71) Applicants: Gerardus Adrianus Petronella Lommerse, Noordwijkerhout (NL); Hendrikus Petrus Lommerse, Lisse (NL)

(72) Inventors: Gerardus Adrianus Petronella Lommerse, Noordwijkerhout (NL); Hendrikus Petrus Lommerse, Lisse (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 16/603,000

(22) Filed: Jan. 13, 2020

(51) Int. Cl.
*A01H 6/04* (2018.01)
*A01H 5/02* (2018.01)

(52) U.S. Cl.
USPC ..... Plt./356.12

(58) Field of Classification Search
USPC ..... Plt./356.12
See application file for complete search history.

*Primary Examiner* — Annette H Para
(74) *Attorney, Agent, or Firm* — C. A. Whealy

(57) ABSTRACT

A new and distinct cultivar of *Allium* plant named 'Avat88', characterized by its upright plant habit with upright flowering stems; vigorous growth habit and moderately rapid growth rate; ensiform yellow green-colored leaves; early and freely flowering habit; numerous light purple-colored flowers arranged on dense inflorescences; long flowering period; and good garden performance.

2 Drawing Sheets

Figure 1:
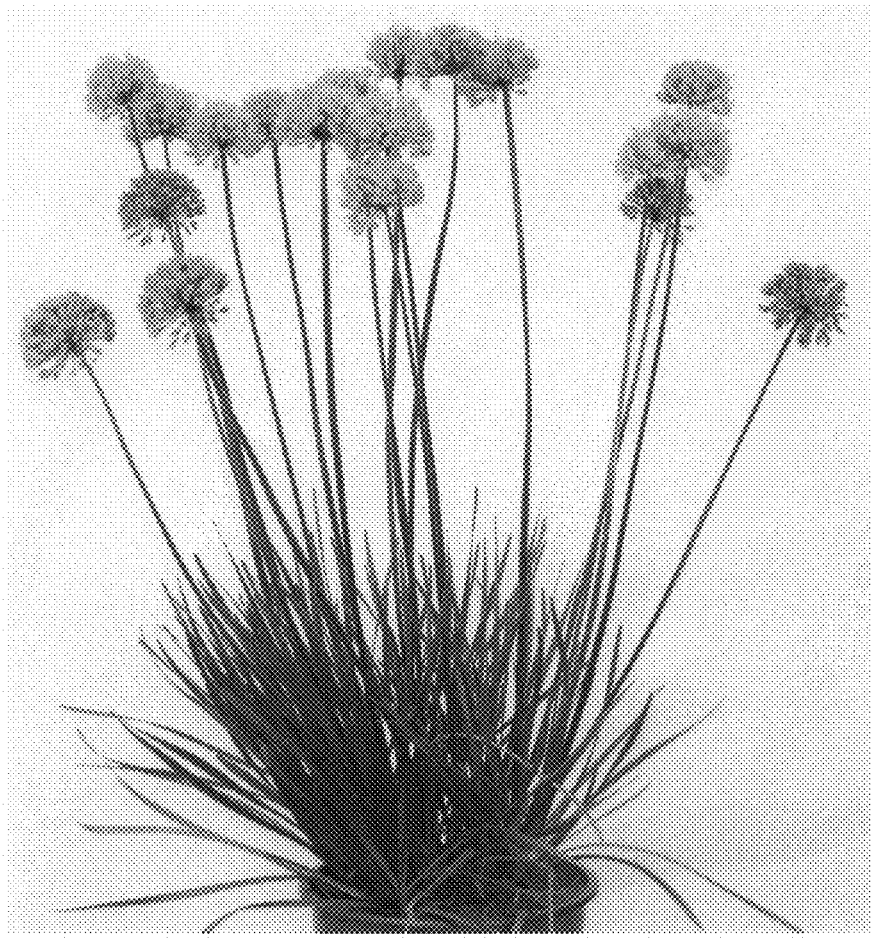

Botanical designation: *Allium tanguticum.*
Cultivar denomination: 'AVAT88'.

BACKGROUND OF THE INVENTION

The present invention relates to a new and distinct cultivar of *Allium* plant, botanically known as *Allium tanguticum* and hereinafter referred to by the name 'Avat88'.

The new *Allium* plant is a naturally-occurring whole plant mutation of *Allium tanguticum* 'Summer Beauty', not patented. The new *Allium* plant was discovered and selected by the Inventors as a single plant from within a population of plants of 'Summer Beauty' in a controlled environment in Lisserbroek, The Netherlands in September, 2017.

Asexual reproduction of the new *Allium* plant by divisions in a controlled environment in Lisserbroek, The Netherlands since September, 2017 has shown that the unique features of this new *Allium* plant are stable and reproduced true to type in successive generations.

SUMMARY OF THE INVENTION

Plants of the new *Allium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Avat88'. These characteristics in combination distinguish 'Avat88' as a new and distinct *Allium* plant:

1. Upright plant habit with upright flowering stems.
2. Vigorous growth habit and moderately rapid growth rate.
3. Ensiform yellow green-colored leaves.

4. Early and freely flowering habit.
5. Numerous light purple-colored flowers arranged on dense inflorescences.
6. Long flowering period.
7. Good garden performance.

Plants of the new *Allium* differ primarily from plants of the mutation parent, 'Summer Beauty', in the following characteristics:

1. Plants of the new *Allium* are taller than plants of 'Summer Beauty'.
2. Plants of the new *Allium* are more freely flowering than plants of 'Summer Beauty'.
3. Plants of the new *Allium* start flowering earlier during the flowering season than plants of 'Summer Beauty'.
4. Plants of the new *Allium* flower four weeks longer during the flowering season than plants of 'Summer Beauty'.

Plants of the new *Allium* can be compared to plants of *Allium hybrida* 'Meisi', not patented. Plants of the new *Allium* differ primarily from plants of 'Meisi' in the following characteristics:

1. Leaves of plants of the new *Allium* are not as coarse as leaves of plants of 'Meisi'.
2. Plants of the new *Allium* start flowering earlier during the flowering season than plants of 'Meisi'.
3. Flowers of plants of the new *Allium* are lighter purple in color than flowers of plants of 'Meisi'.

Plants of the new *Allium* can also be compared to plants of *Allium hybrida* 'Millennium', not patented. Plants of the new *Allium* differ primarily from plants of 'Millennium' in the following characteristics:

1. Plants of the new *Allium* are more freely flowering than plants of 'Millennium'.
2. Plants of the new *Allium* start flowering earlier during the flowering season than plants of 'Millennium'.

3. Plants of the new *Allium* flower for a longer period of time during the flowering season than plants of 'Millennium'.
4. Flowers of plants of the new *Allium* are lighter purple in color than flowers of plants of 'Millennium'.

BRIEF DESCRIPTION OF THE PHOTOGRAPHS

The accompanying colored photographs illustrate the overall appearance of the new *Allium* plant showing the colors as true as it is reasonably possible to obtain in colored reproductions of this type. Colors in the photographs may differ slightly from the color values cited in the detailed botanical description which accurately describe the colors of the new *Allium* plant.

The photograph on the first sheet (FIG. 1 of 2) is a side perspective view of typical flowering plant of 'Avat88' grown in a container.

Figure 2:
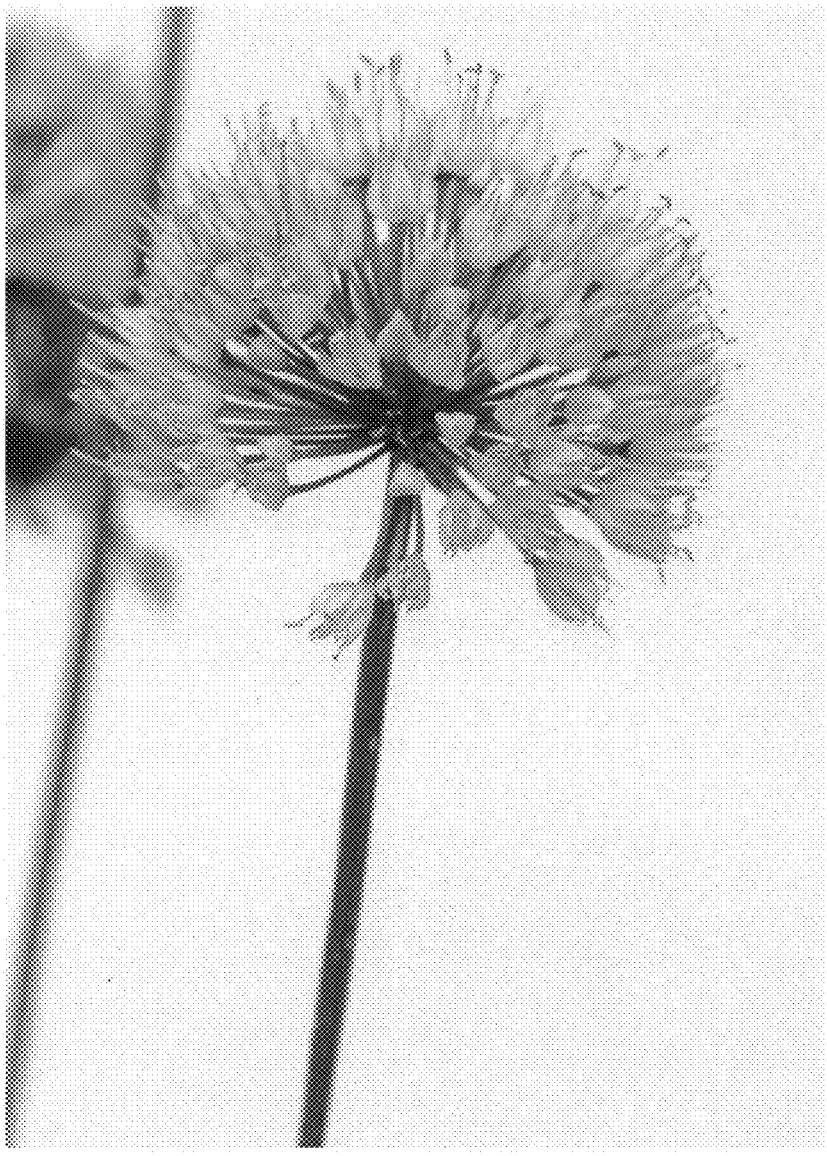

The photograph on the second sheet (FIG. 2 of 2) is a close-up view of a typical inflorescence of 'Avat88'.

DETAILED BOTANICAL DESCRIPTION

The aforementioned photographs and following observations, measurements and values describe plants grown during the summer in 19-cm containers in an outdoor nursery in Lisserbroek, The Netherlands and under cultural practices typical of commercial *Allium* production. During the production of the plants, day temperatures ranged from 16° C. to 40° C. and night temperatures ranged from 8° C. to 24° C. Plants were five months old when the photographs and description were taken. In the following description, color references are made to The Royal Horticultural Society Colour Chart, 2015 Edition, except where general terms of ordinary dictionary significance are used.

Botanical classification: *Allium tanguticum* 'Avat88'.

Parentage: Naturally-occurring whole plant mutation of *Allium tanguticum* 'Summer Beauty', not patented.

Propagation:

*Type*.—By divisions.

*Time to produce a rooted young plant, summer*.—About 13 weeks at ambient temperatures about 20° C.

*Root description*.—Medium in thickness; slightly fleshy; typically greyed white in color, actual color of the roots is dependent on substrate composition, water quality, fertilizer type and formulation, substrate temperature and physiological age of roots.

*Rooting habit*.—Freely branching; dense.

*Bulbs*.—To date, bulb development has not been observed on plants of the new *Allium*.

Plant description:

*Plant and growth habit*.—Herbaceous perennial typically grown as a garden plant; upright plant habit, overall plant shape, broadly obovate; vigorous growth habit and moderate growth rate; globular basal rosette of leaves with upright flowering stems.

*Plant height, soil level to top of foliar plane*.—About 29 cm.

*Plant height, soil level to top of floral plane*.—About 59.4 cm.

*Plant width* (*spread*).—About 52.5 cm.

Leaf description:

*Arrangement*.—Leaves are arranged in basal rosettes with about 8 to 15 leaves per rosette; leaves sheathing and sessile.

*Length*.—About 27.7 cm.

*Width*.—About 6 mm to 8 mm.

*Shape*.—Ensiform, slightly concave and axially twisting.

*Apex*.—Acute.

*Base*.—Sheathing.

*Margin*.—Entire, not undulate.

*Texture and luster, upper and lower surfaces*.—Smooth, glabrous; slightly to moderately glossy.

*Venation pattern*.—Parallel.

*Color*.—Developing leaves, upper and lower surfaces: Close to 143C. Fully developed leaves, upper and lower surfaces: Slightly darker than between 143A and 144A.

*Leaf sheaths*.—Length: About 4.1 cm. Diameter: About 1.4 cm. Texture and luster, upper and lower surfaces: Smooth, glabrous; slightly to moderately glossy. Color, upper and lower surfaces: Close to NN155D.

Flower description:

*Flower type, arrangement and habit*.—Single rotate flowers arranged on dense umbels; umbels flattened globular in shape; freely flowering habit with about 130 flowers developing per inflorescence and about 2,500 flowers developing per plant during the flowering season; flowers face upright to outwardly depending on position on the umbel.

*Natural flowering season*.—Plants flower from July into September in The Netherlands; plants begin flowering about four months after planting rooted young plants.

*Flower longevity on the plant*.—Individual flowers last about 3.5 weeks on the plant; flowers persistent.

*Fragrance*.—Faint; sweet, onion-like.

*Flower buds*.—Length: About 6 mm. Diameter: About 4 mm. Shape: Obovate. Texture and luster: Smooth, glabrous; slightly glossy. Color: Close to 76B, fading towards the base to closer to 76D.

*Inflorescence height*.—About 4.5 cm.

*Inflorescence diameter*.—About 6 cm.

*Flower diameter*.—About 9 mm by 9 mm.

*Flower depth*.—About 1.1 cm.

*Tepals*.—Quantity and arrangement: Six arranged in two whorls. Upper whorl of tepals: Length: About 7 mm. Width: About 2 mm. Shape: Ovate, concave. Apex: Bluntly acute. Base: Broadly cuneate. Margin: Entire, not undulate. Texture and luster, upper surface: Smooth, glabrous; matte. Texture and luster, lower surface: Smooth, glabrous; slightly glossy. Color: When opening, upper and lower surfaces: Close to between 76D and N155A; central band, close to 76A. Fully opened, upper and lower surfaces: Close to between 76D and N155A; central band, close to 76A; venation, close to 76A; color becoming closer to 72D with development. Upper whorl of tepals: Length: About 5.5 mm. Width: About 2 mm. Shape: Ovate, concave. Apex: Bluntly acute. Base: Broadly cuneate. Margin: Entire, not undulate. Texture and luster, upper surface: Smooth, glabrous; matte. Texture and luster, lower surface: Smooth, glabrous; slightly glossy. Color: When opening, upper surface: Close to between 76D and N155A; distally, close to 76C. When opening, lower surface: Close to between 76D and N155A; distally, close to 76A. Fully opened, upper surface: Close to between 76D and N155A; distally, close to 76C;

venation, similar to lamina colors; color becoming closer to 72D with development. Fully opened, lower surface: Close to between 76D and N155A; distally, close to 76A; similar to lamina colors; color becoming closer to 72D with development.

*Scapes*.—Length: About 53.2 cm. Diameter: About 3.5 mm by 6 mm. Aspect: About 22.5° from vertical. Strength: Strong. Texture and luster: Smooth, glabrous; glossy. Color: Close to 144A.

*Pedicels*.—Length: About 2 cm. Diameter: About 0.8 mm. Aspect: Vertical to about 125° from vertical depending on position on umbel. Strength: Strong. Texture and luster: Smooth, glabrous; moderately glossy. Color: Close to 144A to 144B.

*Inflorescence bracts*.—Arrangement: Subtending the tepals and tri-parted. Length: About 1.2 cm. Width: About 6 mm. Texture: Papery. Color: Close to 197D.

*Reproductive organs*.—Stamens: Quantity per flower: Six. Filament length: About 9 mm. Filament color: Close to 76B. Anther shape: Basifixed, oblong. Anther size: About 0.8 mm by 1.5 mm. Anther color: Close to N77B. Pollen amount: Scarce. Pollen color: Close to 202D. Pistils: Quantity per flower: One. Pistil length: About 5 mm. Style length: About 3 mm. Style color: Close to 76B. Stigma size: About 0.2 mm by 0.5 mm. Stigma shape: Pointed. Stigma color: Close to 76D. Ovary color: Close to 76B.

*Seeds and fruits*.—To date, seed and fruit production have not been observed on plants of the new *Allium*.

Pathogen & pest resistance: Plants of the new *Allium* have not been observed to be resistant to pathogens and pests common to *Allium* plants.

Garden performance: Plants of the new *Allium* have exhibited good tolerance to rain, wind and temperatures ranging from about −23° C. to about 40° C. and to be suitable for USDA Hardiness Zones 5 to 10.

It is claimed:

1. A new and distinct *Allium* plant named 'Avat88' as illustrated and described.

* * * * *